United States Patent [19]
Gonella et al.

[11] Patent Number: 5,849,725
[45] Date of Patent: Dec. 15, 1998

[54] PHOSPHORYLATED DERIVATIVES OF COMPOSITIONS HAVING ANTI-INFLAMMATORY OR ANALGESIC ACTIVITY AND A METHOD FOR THE PREPARATION THEREOF

[75] Inventors: Jacques Gonella, Muttenz, Switzerland; Alberto Reiner, Como, Italy

[73] Assignee: Wilton Licensing, AG, Hergiswill NW, Switzerland

[21] Appl. No.: 505,139

[22] Filed: Jul. 21, 1995

[30] Foreign Application Priority Data

Jul. 22, 1994 [IT] Italy ................................ MI94A01555

[51] Int. Cl.⁶ .............................. C07F 9/12; A61K 31/66
[52] U.S. Cl. ............................ 514/80; 514/119; 548/113; 558/170
[58] Field of Search .............................. 558/170; 514/80, 514/119; 548/113

[56] References Cited

FOREIGN PATENT DOCUMENTS

| 084822 | 8/1983 | European Pat. Off. . |
| 2508044 | 12/1982 | France . |
| 2683528 | 5/1993 | France . |
| 2641526 | 1/1978 | Germany . |

OTHER PUBLICATIONS

Lotlikar, Biochem. J. 120 3/661 (1970).

*Primary Examiner*—Robert Gerstl
*Attorney, Agent, or Firm*—Michael N. Meller

[57] ABSTRACT

The principal activity of the amides of ethanol-β-aminophosphoric acid with active moieties having anti-inflammatory and analgesic activity (FANS) remains substantially unchanged but they have considerably lower toxicity particularly in terms of damage to the stomach.

The method for their preparation is also described.

7 Claims, No Drawings

PHOSPHORYLATED DERIVATIVES OF COMPOSITIONS HAVING ANTI-INFLAMMATORY OR ANALGESIC ACTIVITY AND A METHOD FOR THE PREPARATION THEREOF

The present invention relates to amides of ethanol-β-aminophosphoric acid with molecular structures having anti-inflammatory and analgesic activity.

These molecular structures are commonly known as FANS and, as well having anti-inflammatory and analgesic activity they have some considerable disadvantages amongst which the principal one is damage to the stomach. Naturally, this is a significant problem in view of the fact that these drugs have to be administered as a long-term treatment.

It is also known that, particularly for some molecules, the activity of FANS is mainly linked to the active isomer under consideration.

The main object of the present invention is to provide derivatives of FANS the analgesic and anti-inflammatory activity of which remain substantially unchanged but which have a considerably lower toxicity, particularly in terms of damage to the stomach.

It has now been found, and constitutes the main subject of the present invention, that this object is substantially achieved by the corresponding amides substituted with a chemical structure having an aliphatic chain of greater or lesser length and terminating with an easily salified acid group of an inorganic nature.

The derivative chemical compounds of the present invention can be represented by the following general formula:

$$Ar-(CH)_n-CO-NH-(CH_2)_m-O-\overset{O}{\underset{\underset{O^- X_2^+}{|}}{P}}-O^- X_1^+ \qquad (I)$$
$$\underset{Z}{|}$$

in which $X_1$ and $X_2$ may simultaneously represent H, that is $X_1=X_2=H$, or $X_1=H$ and $X_2$ represents an inorganic ion such as, for example, Na, K, Ca, Mg, Al and the like, used as salifiers, or pharmacologically active and non-toxic organic bases also comprising basic amino-acids such as, for example, lysine, arginine, ornithine, or basic cyclic compounds such as, for example, morpholine, aminopyridine and the like, or quarternary organic bases such as, for example, cetyl trimethylammonium or benzyl trimethylammoniumm derivatives; Z represents H or a lower alkyl group; m varies between 0 and 2; n varies between 0 and 2 and Ar represents the residue of an anti-inflammatory and/or analgesic compound of the FANS type.

More specifically and as regards the possible substituents, the preferred compounds of the present invention are the following:

for: n = 1   Z = CH₃   M = 2

[A_r] represents

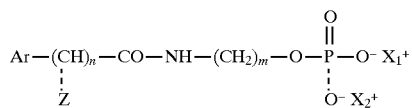

aromatic residue of the compound Ibuprofen

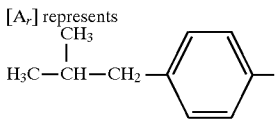

aromatic residue of the compound Naproxen

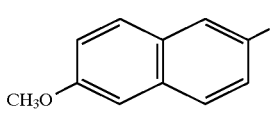

aromatic residue of the compound Flurbiprofen

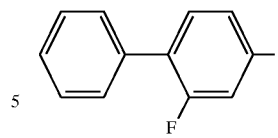

aromatic residue of the compound Ketoprofen

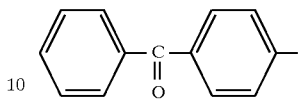

for:   n = 1   Z = (CH₃—CH₂—)   m = 2
[A_r] represents:

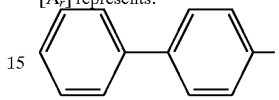

aromatic residue relating to diphenylethyl acetic acid for:   n = 1   Z = H   m = 2
[A_r] represents

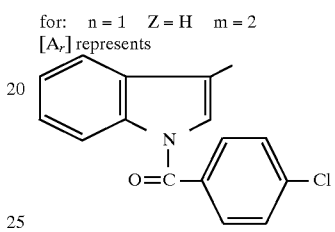

aromatic residue relating to nidometracine for n = 0   m = 2
[A_r] represents

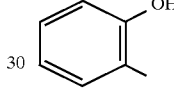

aromatic residue relating to salicylic acid for n = 0   m = 2
[A_r] represents:

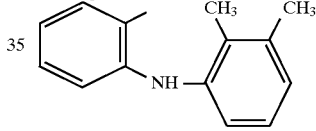

aromatic residue relating to mefenamic acid

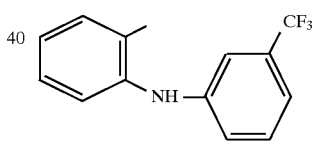

aromatic residue relating to flufenamic acid

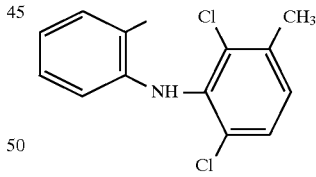

aromatic residue relating to meclofenamic acid

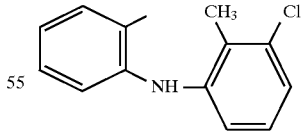

aromatic residue relating to tolfenamic acid for: Z = H   n = 1   m = 2
[A_r] represents

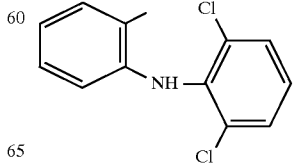

aromatic residue relating to diclofenac

A further subject of the present invention is the method for the preparation of the compounds of Formula (I), the method being characterized by the steps of:

a) the preparation of a functionally reactive derivative selected from a chloride and a mixed anhydride of the desired FANS, b) reaction in an alkaline environment between an organic or inorganic salt of β-amino-ethanephosphoric acid and the functional derivative of the FANS, and c) possibly, the production of a pharmaceutically acceptable organic or inorganic salt (according to the meaning of $X_2$) of the amide produced under normal salifying conditions.

The general scheme for the synthesis for producing the amide derivatives of ethanol-β-aminophosphoric acid thus provides for a first step with the preferred use of chlorination of the FANS with thionyl chloride, or with the formation of a mixed anhydride between the FANS and ethyl chloroformate or ethylbenzyl chloroformate.

The second step makes use of a reaction in an alkaline environment between the sodium salt or another inorganic or organic salt of β-aminoethanephosphoric acid and the chloride or mixed anhydride of the FANS.

The third step describes the possible production of the respective sodium salt or another therapeutically acceptable organic salt of the finished product.

The preparation of (RS) para-iso-butylphenylpropionamido-ethanephosphoric acid as well as of its monosodium salt are therefore described below as non-limiting examples; the same preparation applied to its active (S) isomer is also described by way of non-limiting example. For other derivatives which can be obtained by a similar method it is preferred, however, to group the physical and chemical data of the finished amide products in a single table since they follow the same synthesis scheme.

EXAMPLE 1

Preparation of the Chloride of (R-S) Para-iso-butylphenylpropionic Acid 135 ml of chloroform, 120 g of (RS) para-iso-butylphenylpropionic acid and 53 ml of thionyl chloride were loaded, in sequence, into a 500 ml flask with stirrer, condenser and thermometer. The solution was heated to a temperature of 80°–85° C. for 3 hours, the reaction being monitored by means of the HCl and $SO_2$ vapours evolved. Upon conclusion of the generation of gases, the solution was concentrated under vacuum to produce a yellow oil which was used directly as such for the subsequent reaction.

EXAMPLE 2

Preparation of (R-S) Para-iso-butylphenylpropionoylamido-ethanephosphoric Acid 300 ml of distilled $H_2O$ and 58.56 g of sodium carbonate were loaded, in sequence, into a glass flask with a condenser, stirrer and thermometer and with an external cooling bath. The temperature was reduced to about 0° C. and the mixture was then added to portions of ethanol-β-amino-phosphoric acid for a total equal to the stoichiometric proportion.

The temperature continued to be kept at about 0° C. and 11.5 g of NaOH dissolved in 50 ml of distilled water and 50 ml of dioxane were added. The temperature, which had to be kept between 0° C. and +5° C., continued to be monitored and half of a solution of 130.72 g of the chloride of para-iso-butylphenylpropionic acid dissolved in 200 mL of dioxane was added slowly dropwise; then another solution of 11.5 g of NaOH dissolved in 50 mL of distilled water was added and, at last, the remaining second half of the solution of the chloride of para-iso-butylphenylpropionic acid in dioxane was added too.

Upon completion of the dropping stage, a suspension was obtained which was stirred for 40 hours to produce a colourless clear solution. This was precipitated with 37% concentrated hydrochloric acid, care being taken to drop it in slowly in order to precipitate para-iso-butylphenylpropionylamido-ethanephosphoric acid which was extracted with 650 ml of ethyl acetate. The organic phase was separated from the aqueous phase and was dried over anhydrous $Na_2SO_4$. It was then filtered and concentrated to dryness under vacuum producing a very dense yellow oil which was used as such for the subsequent reaction.

EXAMPLE 3

Preparation of the (R-S) Para-iso-butylphenylpropionylamino-ethanephosphoric Monosodium Salt 187 g of para-iso-butylphenylpropionoylamino-ethanephosphoric acid dispersed in 400 ml of distilled water were loaded into a glass flask.

33.4 g of sodium bicarbonate and 150 ml of isopropyl alcohol were then added, all with mechanical stirring.

A perfect solution was produced and was then concentrated to dryness under vacuum and then taken up by crushing in ethyl ether to produce a crystalline product which could be filtered and dried under vacuum at 50° C. 146.1 g of the sodium salt of (R-S) para-iso-butylphenylpropionoylamido-ethanephosphoric acid was obtained and had the following physical and chemical characteristics:

Appearance: white crystalline solid

Melting point: 151°–153°

Potentiometric titre (0.1N $HClO_4$ in $CH_3COOH$)=100.6%

TLC (90 $CH_3OH$/15 30% $NH_4OH$): Rf 0.5

Water content (K.F.)=0.2%

HPLC (starting acid impurity) 0.62% of p.iso-butylphenylpropionic acid

With the use of the synthesis methods described above in Examples 1, 2 and 3 for the biologically active (S) para-iso-butylphenylpropionic isomer, a finished product of the (S) para-iso-butylphenylpropionoylamido-ethanephosphoric monosodium salt with the following physical and chemical characteristics was produced:

Appearance: white crystalline solid

Melting point: 155°–157°

Water content (K.F.) 2.8% (and in methanol)

Potentiometric titre: (0.1N $HClO_4$ in glacial $CH_3COOH$) =100.6%

TLC=single spot Rf=0.6

HPLC (starting acid impurity) 0.62 of (S) para-iso-butylphenylpropionic acid

The following new derivatives, which are listed below as non-limiting examples, were obtained by applying the synthesis schemes described in Examples 1, 2 and 3 to (RS) and (S) para-iso-butylpropionic acid and their analytical characteristics are grouped in Table 1:

Compound 1: (S) sodium 2-(6-methoxy-2-naphthyl) propionoylamidoethanephosphate

Compound 2: sodium 2-fluoromethyl-(1-1'biphenyl) propionoylamidoethanephosphate

Compound 3: sodium 2-(3-benzylphenyl) propionamidoethanephosphate

Compound 4: sodium 2-(4-biphenyl) butyramidoethanephosphate

Compound 5: sodium 1-(p.-chlorobenzoyl)-5-methoxy, 2-methylindolo-3-indoyl acetamidoethanephosphate Compound 6: sodium 2-hydroxybenzoyl-amidoethanephosphate bases selected from the group consisting of cetyl trimethylammonium and benzyl trimethylammonium derivatives;

$n = 1$, $Z = CH_3$ and $m = 2$,
Ar represents

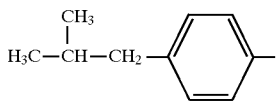

aromatic residue of the compound Ibuprofen

TABLE 1

| Compound | Appearance | Melting Point (Tottoli) | Potentiometric Titre | $H_2O$ Content | TLC 90 $CH_3$ 15 30% $NH_4OH$ | HPLC starting acid impurity | pH 1% $H_2O$ |
|---|---|---|---|---|---|---|---|
| 1 | yellow crystalline solid | 158°/160° | 94.5% | 2.95 | Rf = 0.6 | 1.1% | 4.12 |
| 2 | white crystals | 160/162 | 96.7% | 2.57 | Rf = 0.41 | 0.40% | 3.93 |
| 3 | white crystals | 126/128 | 96.2% | 2.8 | Rf = 0.7 | 1.8% | 4.40 |
| 4 | yellow crystals | 144/146 | 94% | 5 | Rf = 0.66 | 1.38% | 6.42 |
| 5 | yellow crystals | 152/159 | 97% | 3.7 | Rf = 0.65 | 0.2% | 5.75 |
| 6 | white crystals | 215/219 | 98% | 9.94 | Rf = 0.5 | 1.1% | 4.94 |

The products produced were subjected to a preliminary pharmacological investigation.

Not only was the toxicity of the compounds greatly improved in comparison with that known for the starting FANS but their activity also seemed to be greater leading, in particular, to therapeutic indices which are certainly better than those expected for the starting acids.

The use of all of the products which have been produced and can be produced chemically as amides of ethanephosphoric acid having anti-inflammatory and analgesic activity is envisaged in the pharmaceutical and veterinary fields in all of the pharmaceutically effective forms, that is, tablets, capsules, sachets, elixirs, suspensions, gels or ointments, medicated plasters, vaginal washes, suppositories, globuli, drops, eyewashes, lyophilized and normal ampules, etc.

The usual vehicles and excipients are used in these compositions and they are prepared by well known techniques.

The doses are in any case within the ranges expected according to by their specific activity and toxicity, generally varying between 0.20 mg and 1.5 g.

We claim:

1. Phosphorylated derivatives of compounds with anti-inflammatory and analgesic activity having the formula:

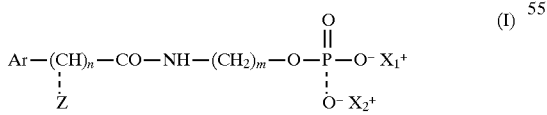

in which $X_1$ and $X_2$ may simultaneously represent H, $X_1=X_2=H$, or $X_1=H$ and $X_2$ represents inorganic ions selected from the group consisting of Na, K, Ca, Mg and used as salifiers, or pharmacologically active and non-toxic organic bases also comprising basic amino-acids selected from the group consisting of lysine and arginine, ornithine, or basic cyclic compounds selected from the group consisting of morpholine and aminopyridine or quarternary organic bases selected from the group consisting of cetyl trimethylammonium and benzyl trimethylammonium derivatives;

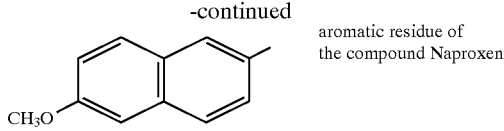

aromatic residue of the compound Naproxen

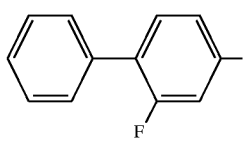

aromatic residue of the compound Flurbiprofen or

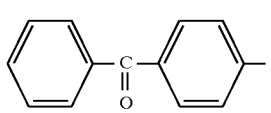

aromatic residue of the compound Ketoprofen.

2. Phosphorylated derivatives of compounds with anti-inflammatory and analgesic activity having the formula:

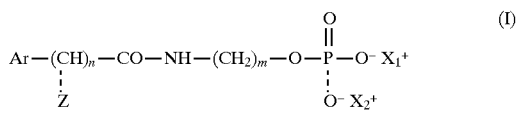

in which $X_1$ and $X_2$ may simultaneously represent H, $X_1=X_2=H$, or $X_1=H$ and $X_2$ represents inorganic ions selected from the group consisting of Na, K, Ca, Mg and used as salifiers, or pharmacologically active and non-toxic organic bases also comprising basic amino-acids selected from the group consisting of lysine and arginine, ornithine, or basic cyclic compounds selected from the group consisting of morpholine and aminopyridine or quarternary organic bases selected from the group consisting of cetyl trimethylammonium and benzyl trimethylammonium derivatives; Z represents H or a lower alkyl group; m varies between 0 and 2; n, varies between 0 and 2 and Ar represents the residue of an anti-inflammatory and/or analgesic compound of the FANS i.e., anti-inflammatory non-steroidal, type wherein when $$n = 1, Z = (CH_3-CH_2-) \text{ and } m = 2,$$

Ar represents:

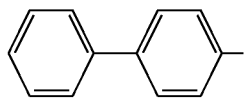
aromatic residue relating to diphenylethyl acetic acid.

3. Phosphorylated derivatives of compounds with anti-inflammatory and analgesic activity having the formula:

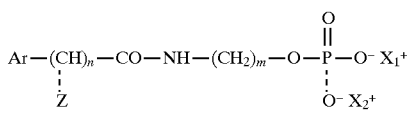

in which $X_1$ and $X_2$ may simultaneously represent H, $X_1=X_2=H$, or $X_1=H$ and $X_2$ represents inorganic ions selected from the group consisting of Na, K, Ca, Mg and used as salifiers, or pharmacologically active and non-toxic organic bases also comprising basic amino-acids selected from the group consisting of lysine and arginine, ornithine, or basic cyclic compounds selected from the group consisting of morpholine and aminopyridine or quarternary organic bases selected from the group consisting of cetyl trimethylammonium and benzyl trimethylammonium derivatives;

$$n = 1, Z = H \text{ and } m = 2,$$

Ar represents

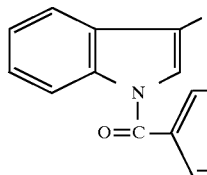
aromatic residue relating to nidometracine.

4. Phosphorylated derivatives of compounds with anti-inflammatory and analgesic activity having the formula:

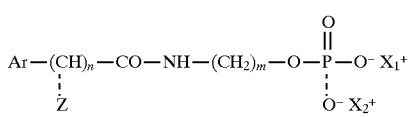

in which $X_1$ and $X_2$ may simultaneously represent H, $X_1=X_2=H$, or $X_1=H$ and $X_2$ represents inorganic ions selected from the group consisting of Na, K, Ca, Mg and used as salifiers, or pharmacologically active and non-toxic organic bases also comprising basic amino-acids selected from the group consisting of lysine and arginine, ornithine, or basic cyclic compounds selected from the group consisting of morpholine and aminopyridine or quarternary organic bases selected from the group consisting of cetyl trimethylammonium and benzyl trimethylammonium derivatives; Z represents H or a lower alkyl group;

$$n = 0, \text{ and } m = 2,$$

Ar represents

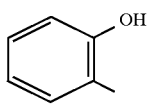
aromatic residue relating to salicylic acid.

5. Phosphorylated derivatives of compounds with anti-inflammatory and analgesic activity having the formula:

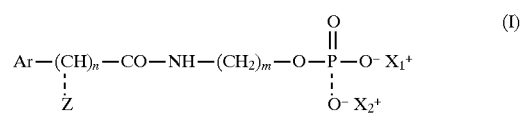

in which $X_1$ and $X_2$ may simultaneously represent H, $X_1=X_2=H$, or $X_1=H$ and $X_2$ represents inorganic ions selected from the group consisting of Na, K, Ca, Mg and used as salifiers, or pharmacologically active and non-toxic organic bases also comprising basic amino-acids selected from the group consisting of lysine and arginine, ornithine, or basic cyclic compounds selected from the group consisting of morpholine and aminopyridine or quarternary organic bases selected from the group consisting of cetyl trimethylammonium and benzyl trimethylammonium derivatives; Z represents H or a lower alkyl group;

$$n = 0 \text{ and } m = 2,$$

[A,] Ar represents

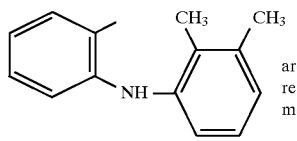
aromatic residue relating to mefenamic acid

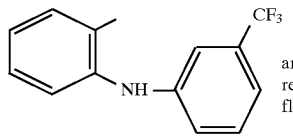
aromatic residue relating to flufenamic acid

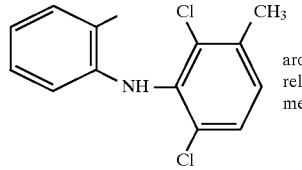
aromatic residue relating to meclofenamic acid

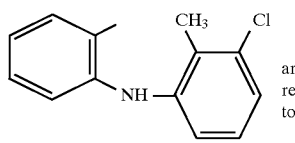
aromatic residue relating to tolfenamic acid

6. Phosphorylated derivatives of compounds with anti-inflammatory and analgesic activity having the formula:

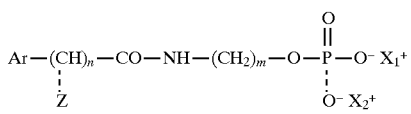

in which $X_1$ and $X_2$ may simultaneously represent H, $X_1=X_2=H$, or $X_1=H$ and $X_2$ represents inorganic ions selected from the group consisting of Na, K, Ca, Mg and used as salifiers, or pharmacologically active and non-toxic organic bases also comprising basic amino-acids selected from the group consisting of lysine and arginine, ornithine, or basic cyclic compounds selected from the group consisting of morpholine and aminopyridine or quarternary organic bases selected from the group consisting of cetyl trimethylammonium and benzyl trimethylammonium derivatives; Z represents H or a lower alkyl group; m varies between 0 and 2; n, varies between 0 and 2 and Ar represents the residue of an anti-inflammatory and/or analgesic compound of the FANS i.e., anti-inflammatory non-steroidal, type wherein when $Z = H$, $n = 1$ and $m = 2$,

[$A_r$] Ar represents

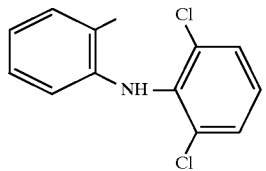

aromatic residue relating to diclofenac

7. A pharmaceutical composition with anti-inflammatory and analgesic activity, characterized in that it contains, as an active ingredient, a pharmaceutically effective amount of a phosphorylated derivative according to any of claims 1 to 6, together with the usual excipients and vehicles.

* * * * *